United States Patent [19]

Prouteau et al.

[11] Patent Number: 4,628,065

[45] Date of Patent: Dec. 9, 1986

[54] PROCESS FOR METHANOL SYNTHESIS FROM CARBON OXIDES AND HYDROGEN IN THE PRESENCE OF A SOLUBLE COPPER AND ZINC CATALYST

[75] Inventors: Didier Prouteau, Aubergenville; Francois Hugues, Nanterre; Yves Chauvin, Le Pecq; Dominique Commereuc, Meudon, all of France

[73] Assignee: Institut Francais du Petrole, Rueil-Malmaison, France

[21] Appl. No.: 747,206

[22] Filed: Jun. 21, 1985

[30] Foreign Application Priority Data

Jun. 21, 1984 [FR] France ................................ 84 09942

[51] Int. Cl.$^4$ ....................... C07C 27/06; C07C 31/04
[52] U.S. Cl. .................................... 518/700; 502/150; 502/152
[58] Field of Search ................................ 518/700, 713

[56] References Cited

U.S. PATENT DOCUMENTS 3,758,417 9/1973 Magoon .
4,031,123 6/1977 Espino et al. ........................ 518/713
4,529,738 7/1985 Sugier et al. ........................ 518/700

FOREIGN PATENT DOCUMENTS 34011 8/1981 European Pat. Off. ............ 518/700

*Primary Examiner*—Howard T. Mars
*Attorney, Agent, or Firm*—Millen & White

[57] ABSTRACT

The invention has as an object a process for methanol synthesis from carbon oxides and hydrogen, performed in an inert liquid medium, in the presence of a catalyst system soluble in the liquid medium.

The catalyst system used according to the invention is obtained by reacting a copper compound, optionally associated with a divalent zinc compound and/or a rare earth compound, with a zinc reducing compound.

20 Claims, No Drawings

PROCESS FOR METHANOL SYNTHESIS FROM CARBON OXIDES AND HYDROGEN IN THE PRESENCE OF A SOLUBLE COPPER AND ZINC CATALYST

The present invention has as an object a process for methanol synthesis from a gas containing hydrogen and carbon monoxide.

BACKGROUND OF THE INVENTION

It has been known for a long time that methanol can be obtained with good selectivity by contacting carbon oxides and hydrogen with a catalyst containing copper and zinc.

This reaction has been applied up to now for manufacturing methanol for chemical uses but, with the prospect of more severe requirements concerning motor fuels, methanol manufacture for use as motor fuel additive has a renewed interest.

The main difficulty to overcome, in particular when carrying out the reaction between carbon monoxide and hydrogen, is the removal of heat generated by this highly exothermic conversion.

The conventional use of heterogeneous catalysts in fixed beds is not favorable to a good heat exchange, since it is liable to produce local overheating detrimental to the activity and to the life-time of the catalyst. Generally this disadvantage is avoided by limiting the conversion rate per run and proceeding with high recycling rates.

SUMMARY OF THE INVENTION

The present invention concerns a process for methanol synthesis from carbon oxides (CO, $CO_2$) and hydrogen, within an inert liquid medium, in the presence of a catalyst soluble in said medium and obtained by interaction of a constituent A, comprising at least one copper compound, with a constituent C comprising at least one zinc compound of zero valency.

The constituent A may optionally further contain, in addition to at least one copper compound, at least one compound B selected from the group consisting of divalent zinc compounds and rare earth metal compounds.

The interaction between constituent A containing at least one copper compound and optionally at least one compound B and constituent C takes place in an inert liquid medium which may be eventually used subsequently as reaction medium or as reaction medium component.

Constituent A of the catalyst comprises at least one copper compound, for example selected from the following compounds: cupric chloride, cuprous chloride, cupric bromide, cuprous bromide cuprous iodide, copper (II) acetylacetonate, cupric or cuprous acetate and, more generally, cupric (I) or (II) carboxylates. Copper (II) carboxylates derived from fatty acids containing 6 to 20 carbon atoms or more, such for example as 2-ethylhexanoate or a mixture of carboxylates of 8,9 and 10 carbon atoms are preferred, in view of their high solubility in hydrocarbon medium.

Constituent A may optionally further contain at least one compound B selected from the group formed of divalent zinc compound and compounds of rare earth metals of atomic numbers from 57 to 71 included. Non limitative examples of divalent zinc compounds are: zinc chloride, zinc bromide, zinc iodide, zinc acetylacetonate, zinc acetate and, more generally, zinc carboxylates. Zinc carboxylates derived from fatty acids containing 6–20 carbon atoms or more, for example 2-ethylhexanoate or a mixture of carboxylates of 8, 9 and 10 carbon atoms are preferred, in view of their high solubility in hydrocarbon medium. Non limitative examples of rare earth metal compounds are: compounds of lanthanum, praseodymium, neodymium, samarium or cerium, these compounnds being, for example, chlorides, acetylacetonates, acetates or other carboxylates. Carboxylates derived from carboxylic acids having 6–20 carbon atoms or more, as for example 2-ethylhexanoate or a mixture of carboxylates having 8, 9 and 10 carbon atoms, are advantageously used.

Constituent C of the catalyst comprises at least one zerovalent zinc reducing compound. Such compounds include those of general formula $ZnR_2$, wherein at least one of radicals R is a monovalent hydrocarbon, the other radical R being either a monovalent hydrocarbon radical or an alkoxy radical, the number of carbon atoms of these radicals being preferably from 1 to 20. However a dialkylzinc with alkyl groups of 1 to 20 carbon atoms, such for example as diethylzinc, is preferred.

The liquid medium wherein constituents A and C are admixed may then be used as the reaction or as a reaction medium component. It must hence be both chemically inert and thermally stable. In this connection, good results are obtained for example with saturated hydrocarbons, particularly paraffinic hydrocarbons, liquid in the reaction conditions, for example heptane, octane, dodecane, hexadecane, or with hydrocarbons mixtures, for example liquid oil cuts or liquid paraffin cuts. Naphthenic hydrocarbons, for example decahydronaphthalene, are also convenient.

But the liquid medium in which are admixed the constituents A and C may also be completely different from the reaction medium to be subsequently used and which will replace it. Thus other solvents than those mentioned above, such as, for example, aromatic hydrocarbons and ethers, for example aliphatic or cyclic ethers, particularly diethylether, dibutylether, tetrahydrofuran and 1.4-dioxane, can be used. When the mixture of constituents A and C has been achieved, the compound to be used as reaction medium can be added. Preferably it will have a boiling point higher than that of the solvent used for the preparation, so that the latter can be easily removed, for example by distillation. For manufacturing the catalyst, at least one copper compound and optionally at least one compound B are, for example, admixed in a first step, without particular care; then the resultant mixture forming constituent A is admixed with constituent C in non-oxidizing atmosphere, for example in inert atmosphere of nitrogen or argon and by using a sufficiently deaerated and dehydrated liquid medium. Constituent A and constituent C may be introduced together, or separately in any order. A preferred operating mode is described hereinafter.

The copper compound of the catalyst is dissolved or suspended in a light paraffinic solvent such as heptane. Optionally a compound B, also diluted in heptane, is added thereto. Then, the resultant mixture is placed in inert argon atmosphere, while effecting several successive vacuum purges.

Constituent C, also handled in inert atmosphere, is then added slowly. A gas evolves from the mixture which undergoes substantial heating. It is preferable to maintain the temperature, during the addition of constituent C, for example between about 0° and about 200° C., preferably between about 50° and about 200° C. When the addition of constituent C has been completed, the desired volume of solvent is added for the reaction, said solvent consisting for example of a liquid paraffinic cut, and the light paraffinic solvent is then evaporated under vacuum. When the mixture has been obtained in another vessel than that used subsequently as the reactor for the synthesis, it is then transferred to the reactor, care then being taken to handle it in the absence of air and of moisture.

The so-obtained catalyst appears as an apparently homogeneous solution of dark-brown color, which can be easily circulated through a pump, for example during its transfer to the reactor. The homogeneous catalyst solution provides for a good thermal diffusion and for a good removal of the heat released by the reaction, which generally are not achieved when using the prior art heterogeneous catalysts.

In the mixture of the copper compound with compound B, the atomic ratio of divalent zinc + rare earth metals to copper may vary to a large extent but is generally from 0:1 to 2:1, preferably from 0:1 to 1:1.

Constituent C is generally used in such amount that the atomic ratio of zerovalent zinc to the sum: copper + divalent zinc + rare earth metals (sum of the metals of constituent A), ranges from 1:1 to 20:1 and preferably from 2:1 to 5:1.

The composition of the synthesis gas mixture is advantageously so selected that the molar ratio "hydrogen/carbon monoxide" in the mixture is from about 0.5/1 to about 20/1 and preferably from about 2/1 to about 10/1. The synthesis gas mixture may also include carbon dioxide in such an amount that the molar ratio $CO_2:CO$ is from 0:1 to 0.1:1 and preferably from 0:1 to 0.05:1 The synthesis gas mixture may also contain a small amount of another gas such for example as methane and nitrogen. The pressure of the hydrogen-carbon oxides synthesis mixture may vary from about atmospheric pressure (0.1 megapascal) to 15 megapascals (MPa) or more. The preferred operating pressure is from 4 MPa to 10 MPa.

The reaction temperature is advantageously from about 100° to about 400° C., but preferably from about 200° to about 300° C.

The hourly space velocity, expressed in volumes of synthesis gas mixture, under normal conditions, fed by volume of liquid phase and per hour (VVH) is usually from about 1 to about 20,000. Preferred VVH values are from about 100 to 10,000.

EXAMPLES

The following examples illustrate the invention but must not be considered in any way as limiting the scope thereof.

EXAMPLE 1

10.625 g of copper 2-ethyl-hexanoate of 8% copper content are introduced in a glass flask of 250 ml capacity. The flask is then purged with argon and 75 ml of dry and distilled heptane are introduced therein. Diethylzinc is then slowly added by means of a hypodermic syringe, in an amount of 4.2 ml, corresponding to an atomic ratio Zn/Cu of 3/1. After 2 hours of reaction a brown homogeneous solution is obtained to which 50 ml of a liquid paraffin cut (initial boiling point: 280° C. under 0.1 MPa), is added. The preparation is completed by removing heptane under vacuum. The catalyst solution is transferred by means of a syringe to a reactor forming part of a micropilot unit which may be operated continuously. This reactor consists of a stainless steel tube of 2 cm inner diameter, of a 100 ml useful volume.

The synthesis gas mixture containing hydrogen and carbon monoxide but free of $CO_2$ and having a molar ratio hydrogen/carbon monoxide of 5, is injected at the bottom of the reactor through a sintered material facilitating its diffusion within the liquid medium, at a flow rate of 40 l (NTP)/h, which corresponds to a VVH of 800 h$^{-1}$. The temperature is set at 290° C. and the pressure maintained at 7.5 MPa by means of a regulator at the unit output.

The results are expressed in terms of:
conversion rate C, in % by mole, defined by:

$$C(\%) = \frac{S + T + CO_2}{CO(\text{input})} \times 100$$

selectivity $S_c$ to products other than $CO_2$, in % by mole, defined by:

$$S_c = \frac{S + T}{S + T + CO_2} \times 100$$

methanol fraction, $F_{CH_3OH}$, in % by mole, defined by:

$$F_{CH_3OH} = \frac{CH_3OH}{S + T} \times 100$$

alcohols fraction, $F_{ROH}$, in % by mole, defined by:

$$F_{ROH} = \frac{T}{S + T} \times 100$$

wherein S is the sum of hydrocarbons, expressed in carbon mole-equivalents:

$$S = C_1 + 2C_2 + 3C_3 + 4C_4 + \ldots$$

and T is the sum of alcohols, expressed in carbon mole-equivalents:

$$T = C_1OH + 2C_2OH + 3C_3OH + \ldots$$

In the above conditions, after 7 hours of run, the results are as follows:

| C = 4.8% | $F_{CH_3OH}$ = 96.3% |
|---|---|
| $S_c$ = 100% | $F_{ROH}$ = 98.9% |

This corresponds to a specific activity of 0.48 gCH$_3$OH/gCu.h. (grams of methanol per gram of copper and per hour).

EXAMPLE 2

The catalyst preparation of example 1 is repeated except that heptane is replaced with tetrahydrofuran, everything else being unchanged. Tetrahydrofuran is then replaced with the same paraffinic cut as used in example 1.

In the same reactor, and with the same operating conditions as in example 1, the following results are obtained:

| | |
|---|---|
| C = 3.6% | $F_{CH_3OH}$ = 93.7% |
| $S_c$ = 100% | $F_{ROH}$ = 97.6% |

This corresponds to a specific activity of 0.35 gCH$_3$OH/gCu.h.

EXAMPLE 3

10.625 g of copper 2-ethylhexanoate having a 8% copper content and 8.750 g of zinc (II) 2-ethylhexanoate having a 9.9% zinc content are introduced in a glass flask of 250 ml. This represents an atomic ratio Zn$^{(II)}$/Cu of 1.01.

The flask is purged with argon and 70 ml of dry and distilled heptane are introduced therein. Then 8.37 ml of diethylzinc are slowly added. They correspond to an atomic ratio:

$$Zn^{(*)}/(Cu+Zn^{II})=2.99$$

50 ml of the liquid paraffin cut used in example 1 are added to the so-obtained homogeneous brown solution, and heptane is removed by treatment under vacuum. The catalyst is then charged in the apparatus described in example 1.

During a first period of 7 hours, the reactor is fed with a synthesis gas of molar composition: H$_2$/CO=5.8, at a flow rate of 40 l (NTP)/h. The temperature is set at 250° C. and the pressure at 7.5 MPa.

The following results are obtained:

| | |
|---|---|
| C = 0.9% | $F_{CH_3OH}$ = 100% |
| $S_c$ = 100% | $F_{ROH}$ = 100% |

This represents a specific activity of 0.09 gCH$_3$OH/gCu.h.

In a second period of 7 hours, synthesis gas of molar composition H$_2$/CO=5.3 is injected at a rate of 35 l (NTP)/h. The temperature is set at 300° C. and the pressure at 7.5 MPa.

The following results are obtained:

| | |
|---|---|
| C = 9.9% | $F_{CH_3OH}$ = 86.8% |
| $S_c$ = 69.8% | $F_{ROH}$ = 97.0% |

This represents a specific activity of 0.56 gCH$_3$OH/g Cu.h.

EXAMPLE 4

10.625 g of copper 2-ethylhexanoate of 8% copper content and 3.1 g of lanthanum 2-ethylhexanoate of 6% lanthanum content, i.e. an atomic ratio La/Cu=0.1, are introduced in a glass flask of 250 ml. The flask is purged with argon and 70 ml of dried and distilled heptane are introduced therein. Then, 4.62 ml of diethylzinc are slowly injected, which corresponds to an atomic ratio Zn/(Cu+La) of 3. Then 50 ml of the liquid paraffin cut used in example 1 are added and heptane is removed by treatment under vacuum. The catalyst is then charged into the apparatus described in example 1.

During a first injection period of 7 hours, a synthesis gas is introduced in the reactor at a rate of 38 l (NTP)h, said gas having a molar composition H$_2$/CO=5.4. The temperature is set at 255° C. and the pressure at 7.5 MPa. The following results are obtained:

| | |
|---|---|
| C = 4.1% | $F_{CH_3OH}$ = 94.6% |
| $S_c$ = 100% | $F_{ROH}$ = 98.4% | i.e. a specific activity of 0.39 gCH$_3$OH/g Cu.h.

In a second period of 7 hours, the synthesis gas is injected at a rate of 36.5 l (NTP)/h. It has a molar composition:H$_2$/CO=5. The temperature is 300° C. and the pressure 7.5 MPa.

The following results are obtained:

| | |
|---|---|
| C = 10.1% | $F_{CH_3OH}$ = 96.3% |
| $S_c$ = 100% | $F_{ROH}$ = 96.3% | i.e. a specific activity of 0.94 gCH$_3$OH/g Cu.h.

In a third period of 7 hours, the synthesis gas is injected at a rate of 36 l (NTP)/h. It has a molar composition:H$_2$/CO=5. The temperature is 250° C. and the pressure 5 MPa. The following results are obtained:

| | |
|---|---|
| C = 3.4% | $F_{CH_3OH}$ = 99.0% |
| $S_c$ = 100% | $F_{ROH}$ = 99.0% | i.e. a specific activity of 0.33 g CH$_3$OH/g Cu.h.

What is claimed as the invention is:

1. In a catalytic process for manufacturing methanol comprising reacting carbon oxides with hydrogen, in an inert liquid medium, the improvement wherein the reaction is conducted in the presence of a catalyst soluble in said medium, said catalyst obtained by interaction of at least one copper compound, with at least one zinc compound of zero valence having the formula ZnR$_2$, wherein each R is a monovalent hydrocarbon or alkoxy with the provision that at least one R is a monovalent hydrocarbon and wherein the interaction of the zerovalent zinc compound with the copper compound is conducted in an inert liquid medium and unnder a non-oxidizing atmosphere.

2. A process according to claim 1, wherein the copper compound is a copper carboxylate.

3. A process according to claim 1, wherein R has 1-20 carbon atoms.

4. A process according to claim 3, wherein each R is alkyl.

5. A process according to claim 4, wherein the zero valent zinc compound is dialkylzinc.

6. A process according to claim 1, wherein the ratio of zero valent zinc/copper ranges from 1:1 to 20:1.

7. A process according to claim 1, wherein the inert liquid medium is a saturated hydrocarbon, saturated hydrocarbon mixture, or a naphthenic hydrocarbon.

8. A process according to claim 1, wherein the reaction is conducted at a temperature from about 100° C. to about 400° C., a pressure from about 0.1 to about 15 MPa, a VVH from about 1 to about 20 000 and a H$_2$/CO ratio from about 0.5/1 to about 30/1.

9. A process according to claim 1, wherein the copper compound is cupric chloride, cuprous chloride, cupric bromide, cuprous bromide, cuprous iodide, copper (II) acetylacetonate, cupric acetate or cuprous acetate.

10. A process according to claim 2, wherein the copper carboxylate is derived from a fatty acid containing 6–20 carbon atoms.

11. A process according to claim 10, wherein the copper carboxylate is a mixture of carboxylates having 8-10 carbon atoms.

12. In a catalytic process for manufacturing methanol comprising reacting carbon oxides with hydrogen in an inert liquid medium, the improvement wherein the reaction is conducted in the presence of a catalyst soluble in said medium, said catalyst obtained by interaction of at least one copper compound, at least one zerovalent zinc compound, and either at least one divalent zinc compound, at least one rare earth metal compound or a mixture thereof, wherein the zerovalent zinc compound has the formula $ZnR_2$, and wherein each R is a monovalent hydrocarbon or alkoxy, with the provision that at least one R is a monovalent hydrocarbon and wherein the interaction of said compounds is conducted in an inert liquid medium and under a non-oxidizing atmosphere.

13. A process according to claim 12, wherein the divalent zinc compound is a zinc carboxylate.

14. A process according to claim 12, wherein the rare earth metal is a rare earth metal carboxylate.

15. A process according to claim 12, wherein the atomic ratio "divalent zinc + rare earth metals/copper" ranges from 0:1 to 2:1.

16. A process according to claim 12, wherein the divalent zinc compound is zinc chloride, zinc bromide, zinc iodide, zinc acetylacetonate or zinc acetate.

17. A process according to claim 13, wherein the zinc carboxylate is a mixture of carboxylates having 8-10 carbon atoms.

18. A process according to claim 12, wherein the rare earth compound is a compound of lanthanum, praseodymium, neodymium, samarium or cerium.

19. A process according to claim 12, wherein the divalent zinc compound is zinc (II) 2-ethylhexanoate.

20. A process according to claim 12, wherein the ratio of zerovalent zinc to the sum of the copper, divalent zinc and rare earth metals A is 2:1 to 5:1.

* * * * *